United States Patent

Helmy

[11] Patent Number: 5,888,230
[45] Date of Patent: Mar. 30, 1999

[54] MODULAR LINER FOR LIMB STUMP PROSTHESIS

[76] Inventor: Nashat N. Helmy, 2035 Ordway Rd., Golden Valley, Minn. 55422

[21] Appl. No.: 831,149

[22] Filed: Apr. 1, 1997

[51] Int. Cl.⁶ ........................................................ A61F 2/78
[52] U.S. Cl. .................................. 623/34; 623/36; 602/62
[58] Field of Search .................................. 623/34, 36, 37, 623/33, 35; 602/62, 63; 264/222, DIG. 30; 425/2

[56] References Cited

U.S. PATENT DOCUMENTS

| | | |
|---|---|---|
| 3,548,420 | 12/1970 | Spence ........................................ 623/37 |
| 3,889,301 | 6/1975 | Bonner, Sr. . |
| 4,432,101 | 2/1984 | Johnson . |
| 4,655,779 | 4/1987 | Janowiak . |
| 4,923,475 | 5/1990 | Gosthnian et al. . |
| 5,108,456 | 4/1992 | Coonan, III . |
| 5,133,776 | 7/1992 | Crowder . |
| 5,139,523 | 8/1992 | Paton et al. . |
| 5,246,464 | 9/1993 | Sabolich . |
| 5,314,497 | 5/1994 | Fay et al. . |
| 5,387,245 | 2/1995 | Fay et al. . |
| 5,405,405 | 4/1995 | Love ........................................... 623/37 |
| 5,464,443 | 11/1995 | Wilson et al. . |
| 5,549,709 | 8/1996 | Caspers ...................................... 623/24 |
| 5,571,208 | 11/1996 | Caspers ...................................... 623/32 |

FOREIGN PATENT DOCUMENTS

| | | | |
|---|---|---|---|
| 0 086 147 A1 | 3/1983 | European Pat. Off. ................. | 623/36 |
| 1739990 A1 | 6/1992 | U.S.S.R. .................................. | 623/36 |

OTHER PUBLICATIONS

Thorndike, Suction Socket Prosthesis for Above–Knee Amputees, American Journal of Surgery, 78(5), 603–613, Nov. 1949.
Rincoe advertisement, Biomechanics, Mar. 1996.

*Primary Examiner*—David H. Willse
*Attorney, Agent, or Firm*—Nawrocki, Rooney & Silvertson, P.A.

[57] ABSTRACT

Apparatus for effecting comfortable fitting of a prosthetic appliance over an amputee's limb stump which has an irregular surface. The apparatus includes a liner surrounding the stump. The liner is, in turn, at least indirectly, connected to the artificial limb. A vacuum pump is provided, the pump serving to draw vacuum at an interface of the stump and an inner wall of the liner, and a plurality of pressure-sensitive transducers are disposed about the stump at locations spaced from each other. The apparatus includes a controller, responsive to pressure reduction sensed by the transducers, to actuate the vacuum pump

11 Claims, 3 Drawing Sheets

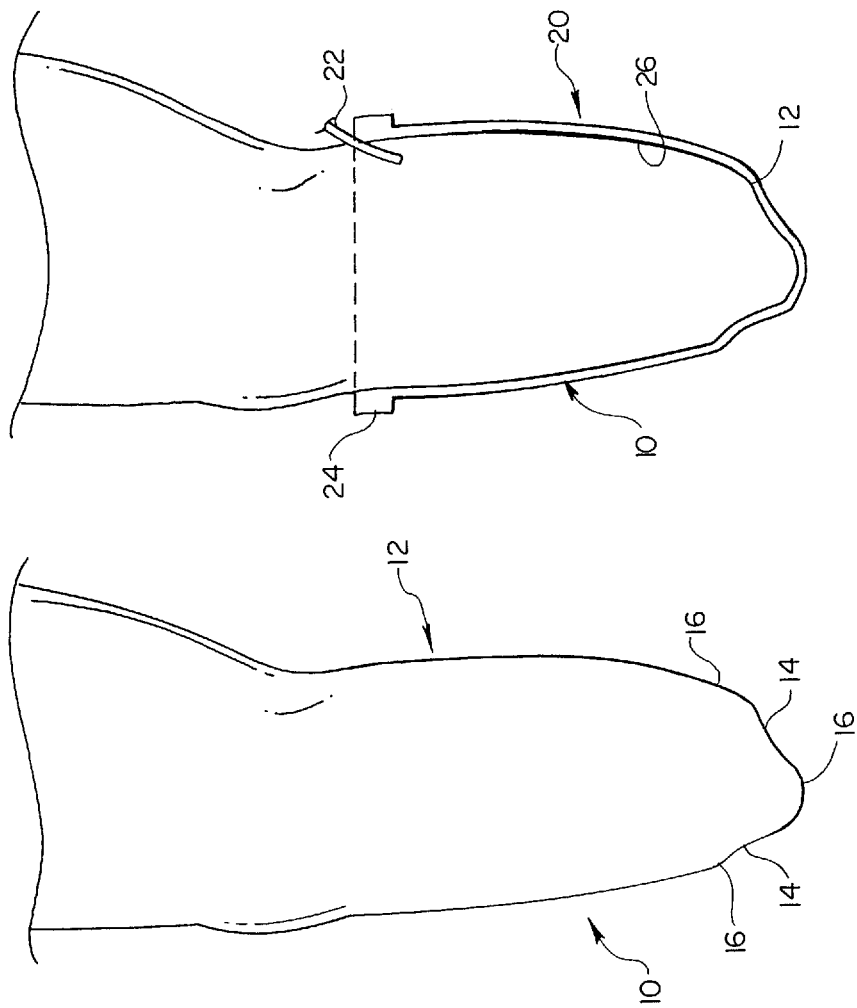

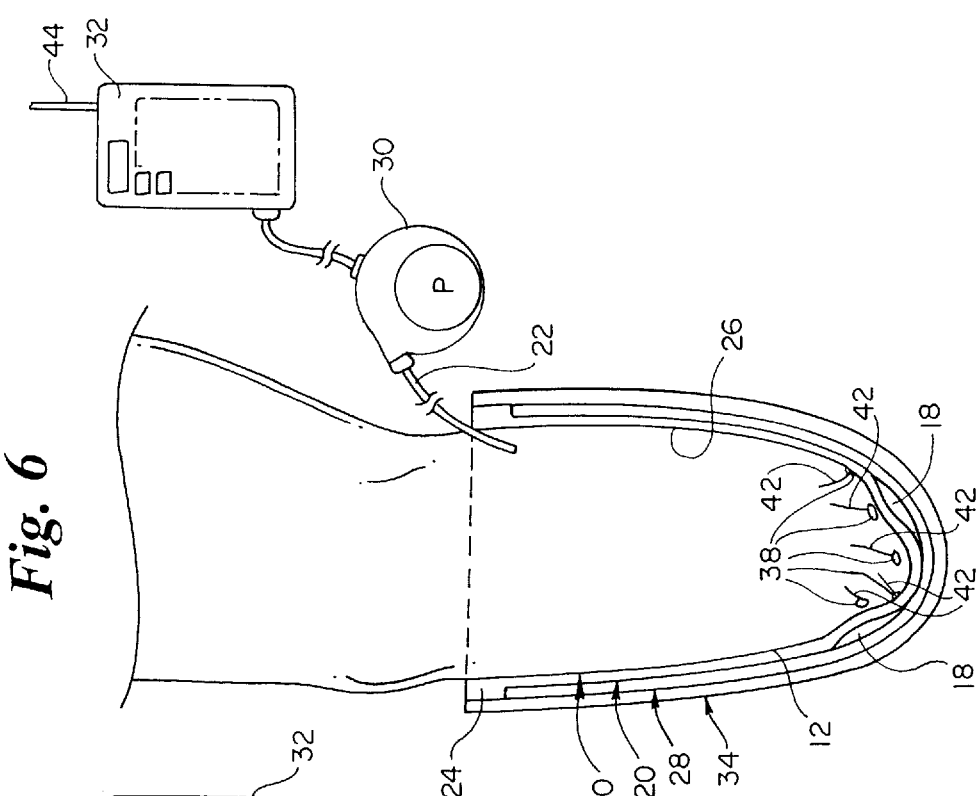
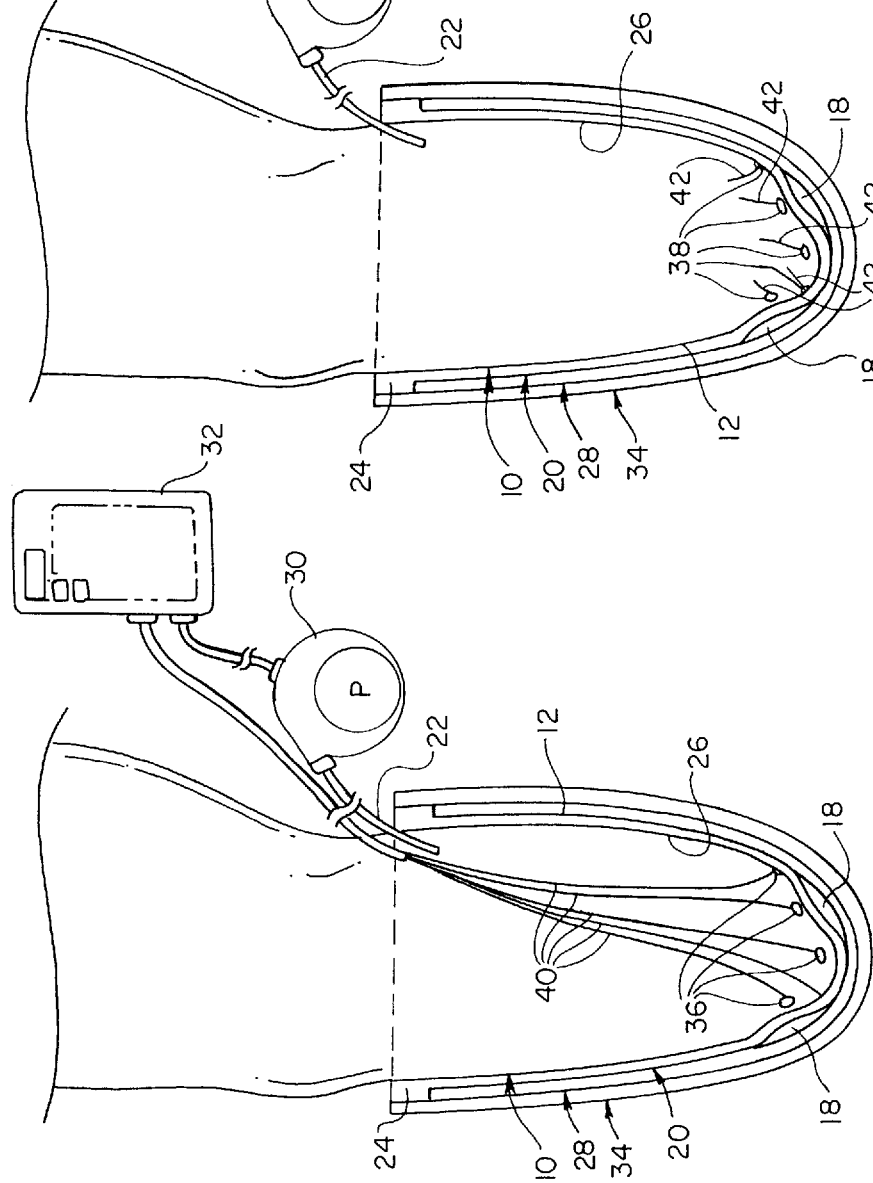

MODULAR LINER FOR LIMB STUMP PROSTHESIS

TECHNICAL FIELD

The present invention is related broadly to the field of prosthetics. More specifically, however, the invention relates to a prosthetic liner for an artificial limb to cover and be attached to the stump of an amputee. The specific focus of the invention is a modular concept for providing a custom-fitted liner for a prosthesis for an amputee's limb, such as a stump extending downwardly from an amputee's knee or from above the knee.

BACKGROUND OF THE INVENTION

Various prosthetic liners are known in the prior art. For example, U.S. Pat. No. 5,446,443 (Wilson et al.) issued on Nov. 7, 1995 for a device characterized as PROSTHETIC DEVICE FOR AMPUTEES. That reference discusses the use of a prosthesis which has a relatively rigid, support shell dimensioned to receive a portion of the residual limb of the amputee. The apparatus also includes a pad member which has a plurality of pouches at least partially filled with fluid. It is intended that the pad member of that reference substantially encircle the residual portion of the amputee's leg with its fluid pouches being positioned adjacent one another about the end along the leg. The pad member having the pouches is, therefore, placed in median engagement with the stump.

U.S. Pat. No. 5,405,405 (Love) issued on Apr. 11, 1995 for an invention entitled PROSTHETIC SOCKET CONTAINING INFLATABLE MEANS. That reference teaches a composite socket member for use with a prosthetic appliance. An outer socket of the device defines an inner cavity generally conforming to the outer surface of the residual limb of the amputee. An inner socket defines an inner cavity which is intended to receive the amputee's residual limb. The inner socket conforms to the shape of the outer socket and, when nested within the cavity of the outer socket, defines an air space between the inner surface of the outer socket and the outer surface of the inner socket. An inflatable bladder is disposed between the inner surface of the outer socket and the outer surface of the inner socket. Means are provided for inflation of the bladder. The movement and rotation stability of the prosthetic appliance is, thereby, controlled.

U.S. Pat. No. 5,387,245 (Fay et al.) issued on Feb. 7, 1995 for a device characterized as an INFLATABLE PROSTHESIS LINER. The apparatus includes a socket having selectively inflatable bladders which enable the prosthesis to be customized to fit an individual patient. A liner having two liner parts is employed to accomplish this goal. One liner part is placed onto the amputee's stump. A prosthetist then determines the region or regions where bladders are needed to provide a comfortable fit. These areas are identified and overlain with an adhesive. The outer liner is then brought into overlying relationship to the inner liner so that the two liner parts adhere to one another along the outlined regions. After inflation of a bladder or bladders, the inner liner conforms to the stump, and the outer liner conforms to the shape of the inner wall of the socket of the appliance. The device can include an annular bladder at the proximal rim of the socket to create a seal in order to maintain a suction within the socket.

U.S. Pat. No. 5,314,497 (Fay et al.) issued on May 24, 1994 for a device characterized as APPARATUS AND METHOD FOR SEALING A LINER TO A PROSTHESIS. The liner of that reference is intended to cushion an amputee's stump when it is placed into a prosthesis socket. In order to accomplish this, the liner includes selectively inflatable bladders or customizing the liner to fit individual patients. The liner is made of two parts. The first is an inner liner and the second is an outer liner. A region or regions where inflation to expand the space between the two liners might be needed are defined and outlined with an adhesive. The inner and outer liner portions adhere to one another along the outlined regions to define bladders. The bladders can then be selectively inflated to conform the outer liner to the shape of the interior wall of the appliance socket.

U.S. Pat. No. 5,246,464 (Sabolich) issued on Sep. 21, 1993 for an apparatus characterized as ARTIFICIAL LIMB WITH ANATOMICALLY CONFIGURED SOCKET. The device of that reference includes a system of inflatable compartments to enable the adjusting of the size and fit of the prosthesis. With the provision of these compartments, the patient may adjust the dimensions of the socket by inflating one or more of the compartments.

U.S. Pat. No. 5,139,523 (Paton et al.) issued on Aug. 18, 1992 for an ARTIFICIAL LIMB SOCKET APPARATUS. The device disclosed by that reference includes a vent provided through a sleeve support for venting the interior of the socket. The reference also teaches the provision of pneumatic chambers to enhance comfort of the amputee.

U.S. Pat. No. 5,133,776 (Crowder) issued on Jul. 28, 1992. The apparatus of that reference is characterized as a PROSTHETIC VOLUME COMPENSATION DEVICE. It includes an air cell or cells which may be placed into an existing prosthesis or included into a newly-fabricated prosthesis. Means are included to allow for manual adjustment of the degree of inflation of the air cell or cells so that changes in volume of the residual limb of the amputee may be compensated for as required. Inflation is accomplished by a fingertip operated pump. A valve is also provided to allow for exhausting air from the air cell.

U.S. Pat. No. 5,108,456 (Coonan, III) issued on Apr. 28, 1992 for a PROSTHETIC APPLIANCE. That appliance includes several inflatable bladders which, when inflated, act against the rigid side walls of the prosthesis member in order to force portions of the socket member side walls inwardly to grip the residual limb of the amputee. Inflation control means are provided and can include a manually-operable air pump. One or more manually-operable air valves are also provided. A valve is used in combination with each of the bladders to allow for exhaust of air from the corresponding bladder.

U.S. Pat. No. 4,923,475 (Gosthnian et al.) issued on May 8, 1990. The device of that reference is characterized as an INFLATABLE LIMB PROSTHESIS WITH PREFORMED INNER SURFACE. The reference teaches a stump-receiving socket and a plurality of inflatable bladders. Means are employed in order to enable one to vary the pressures within the bladders. The bladders are made of a relatively soft, flexible membrane material such as polyurethane. The membranes are located adjacent the weight-bearing portions of the stump to provide a relatively soft, uniform surface to support the stump. The various pressures in the bladders are independent of each other, and regulation by the user is envisioned.

U.S. Pat. No. 4,655,779 (Janowiak) issued on Apr. 7, 1987 for an AIR SYSTEM PROSTHESIS FOR AMPUTEES. The system invention includes a hollow body with stiff peripheral walls and an open end and a cup-shaped partition defining, with the walls, a first socket. The system also includes a second socket having stiff peripheral walls, the second socket being snugly nested within the first socket. The second socket includes spaced apart inner and outer walls with cup-shaped closed ends interconnected and hermetically sealed at their outer ends. A continuous air chamber between the inner and outer walls is, thereby, defined. A manually-operated air pump and pressure relief valve are mounted on the outer wall. Pressurized air can, thereby, be selectively introduced into the chamber and selectively exhausted therefrom.

U.S. Pat. No. 4,432,101 (Johnson) issued on Feb. 21, 1984 for a CUSHIONING PATELLAR SUPPORT DEVICE. The device of that reference includes an inflatable/deflatable bag which is insertable in an upper front portion of a prosthesis. A quick disconnect, hand-operable pump enables the user of the prosthesis to adjust the degree of bag inflation.

U.S. Pat. No. 3,889,301 (Bonner, Sr.) issued on Jun. 17, 1975 for a THERAPEUTIC STUMP TREATING AIR SAC PROSTHESIS. An air sac is provided to surround the amputee's leg stump. The sac, in turn, is surrounded by a casing which confines the pressure of the air sac inwardly against the stump. The distal end of the air sac is supported around and beneath the patient's stump. Means, between the air sac and the casing, are provided to distort the surface of the air sac and give it vertical stability with respect to supporting means.

A foot or partial leg prosthetic includes an artificial limb portion to simulate the natural limb of the amputee which has been removed. The prosthetic does, however, also include means for mating the artificial limb portion to the residual limb of the amputee.

In accomplishing this function, it is important to consider comfort of the prosthetic user. In fact, in many cases, the issue is not only comfort, but also minimization of irritation to the stump. Where the amputee is a diabetic, rubbing can create a blister and infection which could lead to the need for further amputations or, in the extreme case, even death. Also, a liner must provide a friendly, pressure-free environment. Otherwise, the stump fluid will be pressurized and cause skin and tissue inflammation.

As will be able to be seen in view of this discussion, a prosthesis liner which is custom-fitted has significant advantages over one which may not be custom-fitted. A problem with custom-fitted liners, however, is that it is costly and time consuming to measure, assemble, and properly fit such an appliance. It is common to make one or more molds of the amputee's stump in the process. Drying and curing of the mold can consume significant portions of time and result in significant delays.

It is to the shortcomings of the prior art as represented by the references discussed hereinbefore and to advantageous dictates of the art that the present invention is directed. It is an improved prosthetic liner which serves to solve many of the problems of the prior art and which considers the positive dictates suggested by the prior art.

SUMMARY OF THE INVENTION

The present invention is an apparatus for fitting a prosthetic appliance to an amputee's limb stump. Typically, such a limb stump has an irregular outer surface. The apparatus includes means for conforming the irregular outer stump surface to an inner surface of a closed end liner which is intended to surround the stump. The inner liner is conformed to the stump by applying a vacuum between the stump and the liner. There are one or more small tubes which enter the upper band portion of the inner liner. By applying vacuum and holding it during fitting of the liner, the thin inner liner will conform to the exact shape of the stump. This inner liner is made of a very soft but tough elastic material which simulates the feeling of skin. It will move and absorb all surface pressures at the bony stump area. The inner liner is reinforced in the axially central portion to restrict movement and creeping. The outer wall surface of the liner is slightly textured and made in such a way to promote adhesion to an intermediate liner.

In a preferred embodiment, probably at least two or more small, flat, thin, gelatinous shims are self-adhered to the inner liner to build up the surface of the stump in such a way as to eliminate irregularities and provide a smooth, uniform curvature. The shims also provide more cushioning where needed. While the inner surface of the liner conforms to stump shape, therefore, the outer surface has a smooth radiused profile.

An intermediate liner is received over the inner liner. The intermediate liner is made of a very soft, compliant material which behaves like a liquid or a gel. This material, however, is quite tough, resilient and energy-absorbing and has elongation in a 1,000 to 3,000% range. The intermediate liner has inner and outer wall surfaces, both of which are textured and designed to promote self-adhesion. This intermediate liner is placed over the inner, vacuum, conforming liner. Thus, it adheres to the shim-radiused outer surface of the inner liner and provides a weight-bearing, energy-absorbing comfort layer.

An outer liner, which will have an inner wall surface designed to promote self-adherence to the intermediate liner, is placed over the now composite liner assembly and becomes an integral part of it. The outer wall of the outer liner is smooth, tough and abrasion-resistant. It will not degrade, tear, or be destroyed when exposed to the socket rigid edge.

Once such custom fitting of an amputee with a liner is completed, the liner conforms to the stump with a soft, fatty tissue-like interior. The liner is, thereby, very friendly to the stump. Nevertheless, the composite liner has a tough, abrasion-resistant, strong, elastomeric outer surface. In addition, the liner can have a mechanism and means to change volume and yet maintain good contact to the stump.

In general, the amputee stump will lose body fluids and get smaller (i.e. circumferentially smaller). When this happens, the amputee can lose contact with the liner and feel a sensation of having lost the prosthetic limb completely as well as having lost the necessary contact to make for a smooth walk. At a minimum, comfort could be lost and dangerous pressure spots could be created. The inner liner can, therefore, be provided with a small tube connected to a miniature vacuum pump. This pump can be activated to suck in the inner wall of the composite liner to continue conformance to the stump. The amputee can control the amount of conformity by controlling how much vacuum is applied. This method will provide a pressure-free environment, and no inflatable bladders which may cause pressure spots are employed.

The present invention is thus an improved apparatus for fitting a prosthetic appliance to a limb stump of an amputee. More specific features and advantages obtained in view of those features will become apparent with reference to the DETAILED DESCRIPTION OF THE INVENTION, appended claims, and the accompanying drawing figures.

BRIEF DESCRIPTION OF THE DRAWINGS

FIG. 1 is a fragmentary side elevational view of a typical limb stump;

FIG. 2 is a simplified sectional view thereof with an inner liner received over the stump;

FIG. 5 is a simplified sectional view thereof with the outer liner applied, and illustrating automatic initiated vacuum taking means; and FIG. 6 is a simplified sectional view showing the composite liner assembly with the vacuum pump and a microprocessor as used in an alternative sensor system.

DETAILED DESCRIPTION OF THE INVENTION

Figure 3:
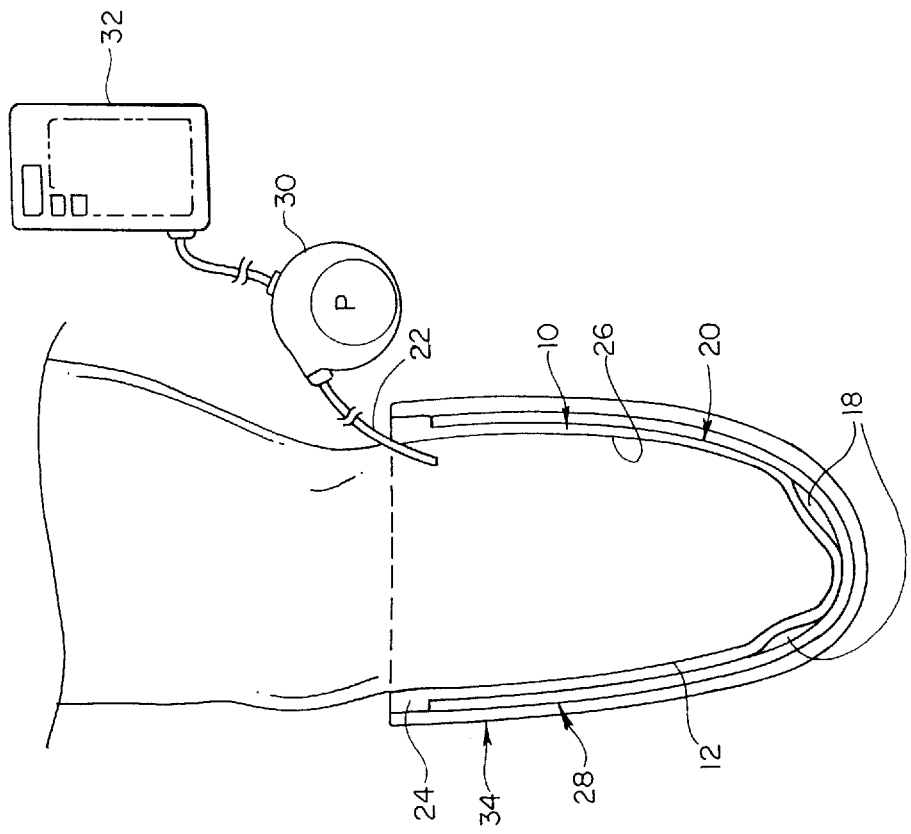
FIG. 3 is a view similar to FIG. 2 illustrating the inner liner received over the stump with a plurality of gelatinous shims applied to the inner liner.

Referring now to the drawings wherein like reference numerals denote like elements throughout the several views, FIG. 1 illustrates a typical stump 10 of an amputee wherein amputation has occurred slightly below the knee. It will be seen that the stump 10 has an irregular surface 12 with some indentations 14 and protrusions 16. It is the provision of comfort to the amputee, in spite of the existence of these indentations 14 and protrusions 16, that the present invention is, in part, directed. Additionally, the invention is also significantly directed to the saving of time and expense incident to the fitting of a custom liner. Typically, the present invention enables the fitting of a custom liner to be accomplished within a short time. This is in contrast to prior art methods and structures where, typically, a minimum of 48 hours, and often in excess of that amount of time, is involved. Further, the present invention enables the custom-fitted liner to be adjusted when there is a loss of volume of the stump 10.

FIG. 3 illustrates a plurality of gelatinous shims 18 having been applied to an inner liner 20 received over the stump 10 in order to fill in indentations 14 in the stump 10 and provide a smoothly radiused surface 12. It will be understood that the preferred embodiment envisions the application of a thin, elastic liner 20, typically made of polyurethane, silicone or other elastomeric material, first being applied to the stump 10. The liner 20 immediately protects the skin surface of the amputee since the thin, elastomeric liner is quite soft and like fat tissue in texture. Such a liner can be provided with a stretchable mesh embedded therein as in Applicant's prior application Ser. No. 08/371,742, which was filed on Jan. 12, 1995 and issued on Jan. 14, 1997 as U.S. Pat. No. 5,593,454.

FIGS. 2–3 illustrate at least one tube or conduit 22 extending axially into the inner liner 20 through an elastic band/seal 24 at an upper end thereof. The tube 22 serves to convey vacuum to between the amputee's stump 10 and the inner wall 26 of the inner liner 20.

Figure 4:
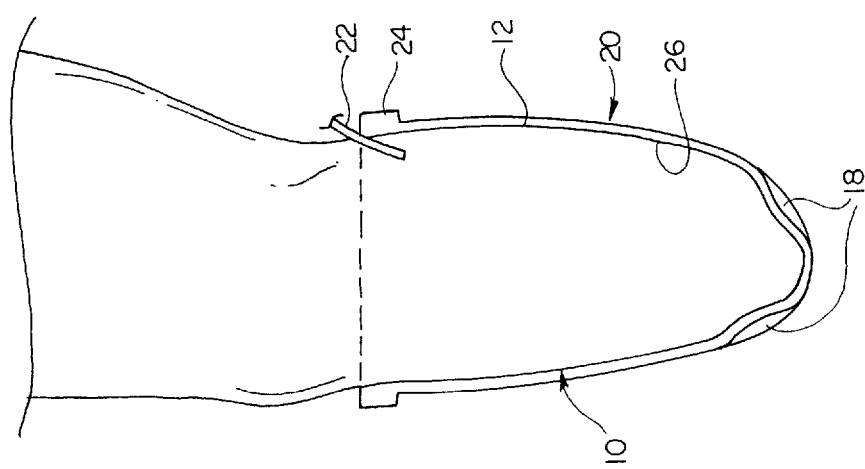
FIG. 4 is a simplified sectional view thereof with an intermediate liner received over the inner liner and an outer liner received over the intermediate liner, and illustrating a vacuum pump and controller.

FIG. 4 illustrates an intermediate liner 28 applied over the inner liner 20. This component 28 would have a gelatinous texture and would serve as the weight-bearing, energy-absorbing and conforming layer to provide a pressure-free environment.

FIG. 4 also illustrates a vacuum pump 30, which is in fluid communication with the tube or tubes 22 in the inner liner 20, and a controller 32, which can be used, in some embodiments, for effecting actuation of the vacuum pump 30. Each tube 22 can have a passageway which affords fluid communication between the inside of the tube 22 and the inner wall 26 of the inner liner 20. Such a passageway enables a vacuum to be taken at the interface between the stump 10 and the inner wall 26 of the inner liner 20. The inner liner 20 is, thereby, drawn into close conformity with the surface 12 of the stump 10. The controller 32 serves to enable volitional generation of the vacuum at the interface between the stump 10 and the inner wall 26 of the inner liner 20.

FIG. 4–6 illustrate an outer liner 34 which encases the full assembly. The outer liner 34 is highly elastic and tough and has a higher modulus and hardness than either of the other liners, although it would typically be made of a polyurethane material also. The outer liner 34 serves to provide abrasion resistance, and it gives form to the composite assembly.

FIG. 5 also illustrates an array of sensors 36 which can be positioned at locations around the stump 10. The sensors 36 can serve to ascertain that there is a reduction in pressure around the stump 10 as a result of volume reduction which might occur because of perspiration or other factors. The sensors 36 serve to transmit to the controller or microprocessor 32, via wires 40, that a reduction in pressure condition has occurred. The microprocessor 32, in turn, will function to actuate the vacuum pump 30, and the generation of additional vacuum will result in the inner wall 26 of the inner liner 20 being drawn into tight engagement with the stump 10. Of course, the other liners will also be drawn in the same direction, since, at this point, the three liners are adhered to one another in a composite arrangement.

In view of the generation of additional vacuum, various adverse effects can be avoided. Particularly, a loose fit which can result in rubbing and infection can be avoided, as can be a complete disengagement of the composite liner from the stump 10.

FIG. 6 illustrates an alternative mechanism for automatically controlling actuation of the vacuum pump 30. The embodiment of FIG. 6, as is true in the case of the embodiment of FIG. 5, employs, typically, a plurality of pressure-sensitive transducers 38 placed at various locations about the stump 10. These transducers 38 sense a reduction in pressure around the stump 10 as a result of a loss of volume within the stump 10. Each transducer 38 in the embodiment of FIG. 5, in turn, has a lead wire 40 which runs to the microprocessor 32. Such a lead wire or lead wires 40 serve to convey information with regard to pressure sensed by the various transducers 38 to the microprocessor 32.

The microprocessor 32, in response to the pressure information sensed and conveyed to the microprocessor 32 from the transducers 38, will effect actuation of the vacuum pump 30. Once a regaining of a desired pressure is sensed as a result of the generation of vacuum, the microprocessor 32 will effect deactuation of the vacuum pump 30.

The embodiment illustrated in FIG. 6 functions in a manner similar to that embodiment shown in FIG. 5. The transducers 38 are not, however, provided with lead wires 40 in this embodiment. Rather, each transducer 38 is provided with a transmitter 42. The microprocessor 32 is, in turn, provided with receivers 44 to accept the transmitted information from the transducers 38. Thereafter, the microprocessor 32 functions in the same manner as in the case of the embodiment of FIG. 5.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. Apparatus for fitting a prosthetic appliance to an amputee's limb stump having an irregular surface, comprising:
   (a) a thin, stretchable inner liner adapted to be received directly over the amputee's stump and conforming thereto;
   (b) a plurality of gelatinous shims adapted to be adhered to said inner liner to fill in indentations in the irregular surface and to provide a smoothly radiused surface;
   (c) a soft intermediate liner adapted to be received over said inner liner having said shims adhered thereto; and
   (d) a highly elastic, abrasion-resistant outer liner adapted to be received over said intermediate liner.

2. Apparatus in accordance with claim 1 further comprising means for taking vacuum at an interface between the amputee's limb stump and an inner wall of said inner liner, wherein said vacuum taking means comprises a vacuum pump in fluid communication with at least one port formed in said inner wall of said inner liner and controller means for actuating said pump.

3. Apparatus in accordance with claim 2 wherein said controller means comprises a microprocessor.

4. Apparatus in accordance with claim 3 further comprising means for ascertaining pressure reduction about said stump.

5. Apparatus in accordance with claim 4 wherein said ascertaining means comprises a plurality of pressure-sensitive transducers adapted to be spaced about the stump at different locations.

6. Apparatus in accordance with claim 5 further comprising means for conveying information from said pressure-sensitive transducers to said microprocessor.

7. Apparatus in accordance with claim 6 wherein said conveying means comprises cable means interconnecting said pressure transducers to said microprocessor.

8. Apparatus in accordance with claim 6 wherein said conveying means comprises a transmitter associated with each transducer, and receiver means at said microprocessor.

9. A custom-fitted, composite liner for fitting a prosthetic appliance to an amputee's limb stump having an irregular surface, comprising:
   (a) a liner adapted to surround the stump;
   (b) a vacuum pump for taking vacuum at an interface of the limb stump and said liner;
   (c) a plurality of pressure-sensitive transducers adapted to be placed about the stump at locations spaced from each other; and
   (d) means, responsive to pressure reduction sensed by said transducers, for actuating said vacuum pump.

10. Apparatus for fitting a prosthetic appliance to an amputee's limb stump, comprising:
    (a) a thin, stretchable inner liner adapted to be received directly over the amputee's stump in engagement therewith and generally conforming thereto;
    (b) an intermediate liner, having a gelatinous texture, receivable over said inner liner;
    (c) an elastic, abrasion-resistant outer liner receivable over said intermediate liner; and
    (d) means for taking vacuum at an interface between the amputee's limb stump and an inner wall of said inner liner.

11. Apparatus in accordance with claim 10 wherein said vacuum taking means comprises a vacuum pump in fluid communication with at least one port formed in said inner wall of said inner liner.

* * * * *